United States Patent [19]

Ceriani et al.

[11] Patent Number: 5,514,558
[45] Date of Patent: * May 7, 1996

[54] HIGHLY SENSTIVE AND SPECIFIC SOLID-PHASE COMPETITIVE ASSAY UTILIZING A FUSION PROTEIN

[75] Inventors: Roberto L. Ceriani; Jerry A. Peterson, both of Lafayette; David J. Larocca, San Leandro, all of Calif.

[73] Assignee: Cancer Research Fund of Contra Costa, Walnut Creek, Calif.

[ * ] Notice: The portion of the term of this patent subsequent to Apr. 8, 2013, has been disclaimed.

[21] Appl. No.: 129,540

[22] Filed: Sep. 30, 1993

Related U.S. Application Data

[62] Division of Ser. No. 46,103, Apr. 8, 1993, which is a continuation of Ser. No. 473,673, Feb. 2, 1990, abandoned.

[51] Int. Cl.$^6$ .................... G01N 33/543; G01N 33/544; G01N 33/563; G01N 33/574
[52] U.S. Cl. .................... 435/7.92; 435/7.23; 435/7.93; 435/810; 436/518; 436/528; 436/64
[58] Field of Search .................... 435/7.23, 7.92, 435/7.93, 188, 810; 436/518, 568, 532, 547, 64, 813, 823

[56] References Cited

U.S. PATENT DOCUMENTS

| | | | |
|---|---|---|---|
| 4,299,426 | 11/1981 | Hales et al. | 303/9.63 |
| 4,299,815 | 11/1981 | Hansen et al. | 436/540 |
| 4,320,109 | 3/1982 | Wolf et al. | 436/542 |
| 4,376,110 | 3/1983 | David et al. | 435/5 |
| 4,378,428 | 3/1983 | Farina et al. | 435/7.23 |
| 4,443,059 | 2/1984 | Chang et al. | 436/512 |
| 4,486,530 | 12/1984 | David et al. | 435/7.91 |
| 4,572,901 | 2/1986 | Ceriani et al. | 436/528 |
| 4,584,268 | 4/1986 | Ceriani et al. | 435/7.23 |
| 4,632,901 | 12/1986 | Valkirs et al. | 435/5 |
| 4,744,175 | 4/1988 | Chang et al. | 435/5 |
| 4,745,055 | 5/1988 | Schenk et al. | 435/7.6 |

OTHER PUBLICATIONS

Henry, J. B., "Clinical Diagnosis and Management by Laboratory Methods", W. B. Saunders Company 1:528 (1979).
Peterhans et al "A Simple Competitive Enzyme–Linked Immunosorbent Using Antigen—Galoctosidase Fusions", Analytical Biochemistry 163 470–475 (1987).
Handl et al, "Enzyme–Linked Immunosorbent Assay for Escherichia Coli Heat–Stable Enterotoxin Type II" Journal of Clinical Microbiology, pp. 1555–1560 (Aug. 1980).
Salinas et al, "Significance of Breast Carcinoma–associated Antigens as a Monitor of Tumor Burden: Characterization by Monoclonal Antibodies", Cancer Res. 47, 907–913, (Feb. 1, 1987).
Imam, A., Laurence, D. J. R. and Neville, A. M. "Isolation And Characterization Of A Major Glyoprotein From Milk––Fat–Globule Membrane Of Human Breast Milk", Biochemistry Journal 193:47–54 (1981).
Ceriani, R. L., Peterson, J. A. and Blank, E. W. "Chapter 16: Breast Cancer Diagnosis With Human Mamm Epithellal Antigens And The Prospective Use Of Antibodies Against Them In Therapy" Mechanisms of Metastasis: Potential Therapeutic Implications. Honn, Powers, Sloane (editors) pp. 235–257 (1986).
A. Ceriani, R. L., et al., "A Novel Serum Assay for Vreast Epithelial Antigen Using a Fusion Protein" Analytical Biochemistry, 201:178–184(1992).
Bowie, J. U. Science vol. 247 pp. 1306–1310, Mar. 1990.

Primary Examiner—Toni R. Scheiner
Assistant Examiner—Nancy J. Parsons
Attorney, Agent, or Firm—Ratner & Prestia

[57] ABSTRACT

An in vitro solid-phase, competitive assay for detecting the presence of a peptide analyte in a biological sample, comprising contacting a fusion protein made of a first peptide and a second peptide to a solid supported first antibody which specifically binds to the first peptide, adding thereto a biological sample containing a peptide analyte, adding a second antibody specifically binding to the analyte and the second peptide, and allowing the second antibody to bind any free analyte present in the sample and the solid supported fusion protein to form analyte-second antibody and solid supported fusion protein-second antibody complexes, and determining the amount of solid supported second antibody present and comparing it to a control. When the amount of peptide analyte in the sample increases the amount of a second antibody bound to the solid support decreases. An optional final addition of an antibody-binding molecule helps detect the antibody-fusion protein complex bound to the solid support. The assay may be utilized for detecting neoplastic antigens from tumors or their metastases by utilizing a fusion protein containing an antigen of an epithelial mammary cell. A kit for detecting the presence of a neoplastic tissue comprises the fusion protein along with a first antibody specifically binding to the first peptide, and a second antibody specifically binding to the second peptide, and optionally a means for detecting the second antibody or fragment thereof, such as an antibody-binding molecule.

51 Claims, No Drawings

HIGHLY SENSTIVE AND SPECIFIC SOLID-PHASE COMPETITIVE ASSAY UTILIZING A FUSION PROTEIN

This application is a divisional application of U.S. application Ser. No. 008/046,103, filed on Apr. 8, 1993, which is a file-wrapper-continuation of U.S. application Ser. No. 7/473,673 filed on Feb. 2, 1990, and now abandoned.

TECHNICAL FIELD

This invention relates to an in vitro solid-phase competitive assay for detecting the presence of an antigenic analyte, or a binding functional fragment or precursor thereof in a biological test sample utilizing a fusion protein of an antigenic peptide or functional fragment thereof and an antigenic analyte or functional fragment or precursor thereof, a solid support-bound antibody raised against the antigenic peptide, an anti-analyte antibody and an antibody binding molecule. The present assay provides higher sensitivity and specificity than other assays.

BACKGROUND OF THE INVENTION

The determination of levels of different antigens in animal and human tissues took a definite turn with the development of immunoassays. The concept on which immunoassays are based is the quantitative binding of an antigen in known quantities to an antibody in equally known quantities, and the binding of this antibody to the antigen to be used as a standard, and a comparison of this to an unknown sample comprising the antigen which will also be bound by the antibody. A key step of these assays is the separation of the bound form of the antibody or the antigen from its unbound form. Many configurations for this reaction have been proposed either as direct immunometric, competitive or displacement assays, and the like. However, to quantitate results it is in general needed to resort to hemagglutination assays, radioimmunoassays, enzyme-linked assays, and the like.

In general, in an immunoassay, a given analyte or antigen present in a animal or human tissue is or may be solubilized for mixing with the immunoassay system, and it is then compared to a solubilized known quantity of the analyte. The most common tissue analyte is blood, and more specifically serum from blood, but urine, cerebro-spinal fluid, different serum preparations and different animal and human tissues are also routinely assayed.

Some of the areas which have most benefited with the advent of immunoassays have been clinical chemistry, endocrinology and oncology. In endocrinology and clinical chemistry enzyme-linked assays and radioimmunoassays have been used to determine levels of hormones, proteins, tumor antigens, and lipid metabolites, among other substances. In the field of oncology blood components, and some times tissue antigens or other molecules, indicate either the appearance of cancer or a pre-cancerous condition in animals or men. These molecules are routinely tested to monitor appearance, relapse, progression or regression of a cancer disease. These antigens or molecules are called cancer markers. For many years markers have been used for this purpose. An example thereof is the oncofetal antigen CEA which is used in the diagnosis of carcinomas, especially those of the colon. Other cancer markers include enzymes such as lactic dehydrogenase and alkaline phosphatase, metabolites such as prostaglandins and polyamines, proteins such as α-fetoprotein and human chorionic gonadotrophin, among others. Immunoassays of these cancer markers are now applied to the diagnosis and follow up of cancer patients.

These assays generally use as standard a partially or fully purified tissue antigen. In some occasions, however, polypeptides are synthesized in the laboratory for use as antigens. The more purified the antigenic substance used as standard for the immunoassay is, the more specific and trustworthy the assay.

A set of membrane-related antigens have been used for the diagnosis of breast cancer. The antigens were originally called human mammary epithelial antigens and antibodies to them were obtained by injection of human milk fat globule (HMFG) membranes to rabbit. These were polyclonal antibodies called anti-human mammary epithelial (anti-HME) antibodies. The antibodies were prepared after repeated absorptions and were found to bind breast epithelial cells selectively. The discovery of this breast epithelial system of antigens opened many new immunologic opportunities in immunohistopathology, serum assays, radioimaging and eventually immunotherapy.

The anti-HME antibodies were shown to bind to breast epithelial cell lines as well as normal breast cells, but not to fibrocytes, vascular cells, and blood cells. HMFG antigens, a special group of breast epithelial antigens (BrE-antigens) originally called human mammary epithelial antigens (HME-antigens), are bound by absorbed anti-serum (anti-HME serum) which were created in the rabbit. These antigens were found to have 150, 70 and 45–48 Kdalton molecular weights as established by affinity chromatography and double antibody immunoprecipitation. A similar system was shown to exist in the mouse. Mouse mammary epithelial antigens may also be detected by absorbed rabbit polyclonal antisera. These antisera also identify in the mouse mammary cell membrane components having molecular weights of 150, 70 and 45–48 Kdaltons. The antigens may be detected in either normal or neoplastic mouse mammary gland. These antigens are not detected in other normal tissue cells or mice.

Other polyclonal antisera were reported to have been produced against a step-purification of HMFG antigens. These antisera are pan-epithelial in nature and reactive only against the non-penetrating glycoprotein (NPGP) complex in contrast to the original anti-HME antibodies that bind the about 45, 70 and 150 kDalton antigens. Although the anti-HME antibodies bind before absorptions to the NPGP complex, anti-HME antibody final preparations do not recognize the NPGP complex as a result of absorptions with non-breast epithelial cells to render anti-HME specific.

HME antigens may be quantitated by an immunoassay in various human breast an non-breast cell lines and in normal breast epithelial cells. High concentrations of HME antigens were found in normal breast epithelial cells and an neoplastic cells. A protease treatment of live breast epithelial cell surfaces releases most antigens therefrom. Similar results show a 48–72 hour time lapse for full reconstitution of the normal breast epithelial cell membrane after digestion.

High levels of HME antigens are found in the sera of nude mice carrying human breast tumors. These antigens can be abolished by surgical removal of the breast tumor. Anti-HME antisera were shown to have certain specificity since other transplantable human tumors such as colon, lung and melanoma, did not increase HME antigen values in mice serum.

The specificity of the assay using anti-HME antigen serum for breast tumors was tested in a nude mouse model carrying transplantable human breast tumors and compared to the specificity of an assay for sialyl transferase levels, which is also a breast cancer marker. The levels of the enzyme which is present on the breast epithelial cell membrane and the HME antigens were measured simultaneously in the sera of nude mice grafted with human breast an non-breast tumors. Breast tumor-bearing mice had elevated levels of both serum markers. However, sialytransferase levels were also elevated in non-breast tumors while HME antigens were not. Upon surgical removal of all tumors, the presence of HME antigens declined precipitously in breast tumor-bearing nude mice while sialytransferase levels remained elevated in both breast and non-breast tumor bearing animals. This is possibly due to surgical trauma and wound healing. The higher specificity of the HME antigen assay was thus proven at least in regard to sialyltransferase, a non-specific co-habitant of the cell membrane together with HME antigens. This indicates again that most, if not all, components of the breast epithelial cell are released into circulation by breast tumors, and that assay specificity, such as is obtained with an assay utilizing HME antigens, may be required to avoid that concurrent ailments or reactions in the tumor host interfere with the values obtained from sera with markers such as sialyltransferase.

HME antigens levels in the sera of breast cancer patients were also obtained using a slightly different radioimmunoassay (U.S. Pat. No. 4,584,268 to Ceriani and Peterson). In this assay, beads coated with polyclonal antibodies were incubated with a patient's serum, then the immobilized antigen was detected with the polyclonal antibodies labeled with biotin, and the latter detected by radiolabeled avidin. The assay was specific for positive cases of breast cancer since the sera of normal subjects, both male and female, suffering from benign diseases of the breast, carcinomas of lung and colon, neuroblastomas and melanomas yielded negative results. In contrast, 25% of Stage I primary breast carcinomas and more than 75% of disseminated breast cancer cases were found to have values above the cut off line.

To date the only complete proof of the existence of HME antigens, or any other BrE-antigens in human sera with elevated values of the breast tumor markers, is provided by a very sensitive technique using in situ radioiodination of the HME antigens bound to an immobilized antibody. In contrast, only a small fraction of breast cancer patients, most of whom had elevated values of BrE antigens, gave positive results when less stringent criteria to detect BrE antigens in sera such as Western blotting were used. Elevated values of the three HMFG antigens detected by anti-HME antibodies were found in the circulation employing the in situ radioiodination approach. These antigens had 150, 70 and 45–48 Kdalton molecular weights in all breast cancer cases. Control sera from normal subjects and patients with colon and lung carcinomas were found to be negative. In addition, the antigen corresponding to one monoclonal antibody (Mc3) was also found in the sera of these patients by the in situ labeling technique. In later work, the Mc3 antigen was found to be associated with immune complexes in breast cancer patients.

Monoclonal antibodies have been used in immunoassays. However, their low binding constants and their restricted specificity are drawbacks to their use. Polyclonal antibodies, on the contrary, combine the specificities for several epitopes of the same antigen. Monoclonal antibodies were originally prepared against HMFG and also against breast tumor cells. As mentioned above, the most immunogenic of the HMFG antigens and breast cells is the NPGP complex, described for its binding to monoclonal antibody Mc1 (also called HMFG-2), and Mc5. This is the only antigen which has thus far been extensively quantitated in serum assays.

The original monoclonal antibodies against HMFG were followed by other monoclonal antibodies created in different laboratories. Immunoassay applied to obtain serum values for primary breast tumor patients and for disseminated disease patients yielded partially positive values in cases of primary breast tumors and small tumor loads. As the tumor load increased, more sera became positive.

The original anti-HMFG monoclonal antibodies, HMFG-1 and HMFG-2 bind to the NPGP complex of the HMFG. These antibodies detected the corresponding antigens in the sera of 30% and 53% of advanced cancer disease cases, respectively. These percentages are low, possibly as a result of the configuration of the assay. In addition, antigenic components with varying molecular weights between 280 and 320 Kdaltons were detected by means of Western blotting in a few of all positive sera detected by the assay. This may indicate either that fragments of the native antigen were found or that the different molecular weight components represent different polymorphic molecules of the antigen. No positives were detected by immunoblotting in any of the normal sera although threshold values were detected by immunoassay.

The DF3 monoclonal antibody also binds to the NPGP complex of the HMFG antigen system. Using this monoclonal antibody a comparison was made between the RIA and ELISA procedures. All yielded increased levels of antigen over the cut off line in more than 70% of the patients with disseminated breast cancer. In contrast thereto, slightly over 5% of normal women had values above the cut off value. Further, 47%, 40% and 27% of patients with ovarian carcinoma pancreatic carcinoma and melanoma were found to have elevated values above the cut-off line whereas ten out of 66 patients with benign liver disease also had elevated values. Patients with visceral breast cancer were found to have a higher frequency of elevated values than those with local or skin recurrences. Results from Western blotting studies were similar to those outlined above for HMFG-1 and HMFG-2 in that a few but not all patients with high immunoassay serum values of the antigen had positive immunoblots.

Another monoclonal antibody, 115D8, raised also against the NPGP complex, was utilized in a sandwich serum assay using the same monoclonal antibody for both layers. The results obtained were similar to the above. About 5% of the samples from normal breasts and benign breast disease showed values above the cut-off line. Breast cancer patients were found positive in 24% of Stage I cases, and in 21%, 43%, and 79% of Stages II through IV cases. 78% positives were found in benign liver disease, kidney disease and in pregnancy cases. A high percentage of ovarian, colorectal, prostate, lung carcinomas, melanoma and lymphoma cases also had elevated values. A good correlation of the marker with the progression or regression of the disease was found in 93% of the cases.

Another early attempt to measure the NPGP complex in circulation was attempted with the F36/22 monoclonal antibody. A similar percentage of positives which were obtained increases with the severity of disease, as also reported in other assays.

A series of monoclonals were created by another laboratory. Out of a latter group, two named W1 and W9 were selected for also binding to the NPGP complex. Elevated levels of the complex were found in 47% of breast cancer patients with visceral metastases, these being favored over localized metastases. This assay was also positive in 4% of normal cases. Other carcinomas such as colorectal, lung, ovarian, and prostate carcinomas show elevated values of the complex in 12 to 60% of the cases. Recently, another assay using a monoclonal antibody, AB13, detected the NPGP complex in approximately half of advanced breast cancer patients.

The monoclonal antibody DF3 has been used in a commercially available double determinant assay called CA 15-3. Levels above the cut-off line in approximately 80% of advanced cancer patients and in only approximately 30% of primary breast cancer cases were found by this assay. Other authors, in contrast, reported only 13% of primary breast tumors and 72% of disseminated tumors to be positive. In a more detailed study only 24% of breast cancer patients were found to have elevated CA 15-3, while 70% to be positive were found in patients with the disseminated disease. A comparison of CEA and CA 15-3 in both primary and disseminated breast cancer samples, proved the latter to be more sensitive. This commercial assay and the ones discussed above against the heavy molecular weight component of the HMFG or NPGP complexes attain percentages of positives (sensitivities) which are at best similar to those originally reported when the presence of the HME-antigens in the circulation of breast cancer patients was established using polyclonal antibodies. The specificities of the assays for the tissue of origin of the tumor are very low (the antigen(s) is almost pan-epithelial), and their specificities for disease conditions are hampered by their high values in hepatic and kidney disease, pregnancy, polymorphic expression of the antigen(s), and the like.

A common feature among the above immunoassays, either utilizing enzymes or radioactivity, is that they indicate a positive correlation between increasing tumor load and higher serum antigen levels. However, a further increase in sensitivity to improve early stage detection of the disease is still necessary. In this regard, an assay using the NPGP complex as a marker and employing the 3E1.2 monoclonal antibody was claimed to have higher sensitivity.

Of a limited number of breast cancer patients up to 68% of early stage patients were found to be positive by this assay whereas only 3% were detected by CA 15-3. The 3E1.2 assay resulted in 18% of positives for benign breast disease resulting then in a low specificity.

Ideally monoclonal antibodies for use in immunoassays would be created against BrE antigen epitopes expressed in breast neoplasias. Alterations in glycoprotein antigens on breast tumor cell membranes have been shown to involve changes in their glycosylation patterns such as substitutions or elongation of oligosaccharide chains without modification of the core sequences. One such monoclonal antibody which is carcinoma specific is B72-3. Its binding to NPGP in benign breast disease tissues was, however, shown later and some normal breast tissue.

All the above monoclonal antibody immunoassays for breast cancer rely on serum levels of the NPGP complex. Other antigens, however, have been explored such as the GP-15, Mc3, and Mc8 antigens. The former is a small molecular weight BrE antigen (16 Kdalton) which is present in the cell membrane. It detects mainly, if not exclusively, breast epithelium that has undergone apocrine metaplasia. It has been found, possibly as a result of its selectivity, in the sera of approximately 40% of breast cancer patients. In addition, a small molecular weight antigen (46 Kdalton) of the HMFG system, already detected by in situ radioiodination in the sera of breast cancer patients was measured by a serum immunoassay using a sandwich configuration with monoclonal antibody Mc8 conjugated to biotin as the probing antibody to be finally detected by $125_{I-labeled}$ avidin (Salinas et al, Cancer Research 47:907(1987)).

Levels of this antigen were detected in breast cancer patients but not in normal subjects, ovarian carcinomas, colon carcinomas or osteosarcomas. Levels of the Mc3–Mc8 antigen, however, were inversely related to the tumor load. Small tumor loads were 95% positive whereas high tumor loads were 65% positive. This fact was explained by the presence of immune complexes against the antigen whose titer is increased in the high tumor load group. The presence of higher level immune complexes may accelerate clearance of the antigen from blood.

Thus, although most of the above assays employing monoclonal antibodies detect the NPGP complex of the HMFG system, many of them may bind to different epitopes. A heterogeneity of epitopic expression may create the relatively small differences seen among different assays. The diffusely pan-epithelial nature of the NPGP complex as a marker was thus established as shown by its high circulating levels found in other carcinomas, melanomas and even in leukemia. The levels obtained varied depending on the units used in different immunoassays. The percent of positives found at different stages of breast cancer are similar to those originally reported with an assay using polyclonal antibodies to other components of the HMFG. An important drawback of the assays based on the detection of the NPGP complex using monoclonal antibodies is that they lack the specificity of polyclonal assays.

A comparison of the specificities of the CEA assay, an assay detecting the NPGP complex using the Mc5 monoclonal antibody in an antigen displacement, and the original polyclonal antibody assay against HME antigens was made. The polyclonal antibody assay showed very high sensitivity and specificity. It yielded negative values for colon, ovarian, pancreatic, laryngeal and endometrial carcinomas, lymphomas, myelomas, melanomas, and leukemias. Only one case of lung carcinoma showed an elevated value. All normal serum controls were negative, thus showing this assay to have high specificity. Positive serum values for both the NPGP complex and CEA assays were not restricted to breast tumor patient's sera.

Another study reported a higher sensitivity for the polyclonal assay of the HME antigens when compared with the monoclonal antibody assay for the NPGP complex and the CEA test. These three assays were compared in terms of their follow-up ability. The response of one polyclonal antibody assay for HME antigens (cut-off 100 ug/ml) to breast cancer relapse and tumor mass change was quantitated and showed a very sensitive response, far above that demonstrated for the Mc5 assay (cut-off 10 ug/ml) for the NPGP complex. In contrast, the CEA assay either responds slowly or not at all. In clinical cases measurable shrinkage of breast tumor mass was obtained and there was a fast decrease of HME antigens corresponding to a decreased tumor mass brought about by irradiation. The levels of the NPGP complexes remained high and the CEA was unresponsive. In summary, the polyclonal assay for HME antigens has a faster response to changes, and is more accurate in predicting objective changes in tumor mass than the other two assays (CEA and NPGP complex).

Previous studies showed the prognostic power for BrE antigens to be up to 90%. A comparison of the ability of these three assays, the CEA, the NPGP complex, and the HME antigen assays, for predicting relapse was performed by comparing the ability to detect relapse within at least two months in breast cancer patients with no evidence of disease (NED) after an increase of 50% in the serum marker base line by the three methods. The HME antigen method showed a predictability of 73% while the CEA and NPGP complex methods had a 46% predictability. Clearly, among the three, the HME antigen method is the one of choice to established prognosis due to its high predictive ability and tis ability to detect early changes in tumor mass fusion proteins have been known and used in immunoassays different from the one described in this patent. Other assays utilizing fusion proteins are known in the art. However, they are all different from the present in vitro competitive heterogeneous assay. Peterhans et al disclose a competitive assay utilizing a fusion protein of β-galactosidase and interferon (Peterhans et al, Analytical Biochemistry 163; 470–475(1987)). In the Peterhans assay, anti-interferon-α monoclonal antibodies are attached to a solid support, the solid supported antibodies are incubated with the fusion protein in the presence of a sample containing interferon and the solid supported material remaining after this step is then incubated in the presence of o-$NO_2$— phenyl-galactopyranose (a substrate for β-galactosidase) to thereby determine the amount of fusion protein bound to the antibody and compared with a similar test conducted in the absence of a test sample. Although this assay is a competitive assay and it relies on the use of a fusion protein of two polypeptides (β-galactosidase and interferon) it only utilizes antibodies to one of the two portions of the fusion protein.

In another case, U.S. Pat. No. 4,745,055 to Schenk et al, human surfactant azoprotein (HSA) was determined using an assay configuration similar to the above and a second assay anti-HSA antibody interfered with the β-galactosidase activity of the fusion protein.

Handl et al disclose another competitive assay relying on the utilization of a fusion protein (Handl et al, J.Clin.Microbiol.26:1555–1560(1988)). The fusion protein in this case is composed of β-galactosidase and enterotoxin II and is bound to a solid support. A test sample containing enterotoxin II is then added and both the fusion protein and the enterotoxin II-containing test sample are allowed to compete for an anti-enterotoxin II polyclonal antibody which is added thereafter. The amount of anti-enterotoxin antibody bound to the solid supported fusion protein is determined by adding anti-antibody immunoglobulin which is labeled with alkaline phosphatase. A substrate for the enzyme alkaline phosphatase is then added to the solid supported material and the amount of conversion obtained is compared with that obtained from a similar test conducted in the absence of the test sample. Although this is also a competitive test utilizing a fusion protein and a sample, both capable of binding antibody against the immunogenic polypeptide, it is different from the one disclosed herein in that the fusion protein is bound to the solid support by the β-galactosidase portion thereof and in that it utilizes solely antibodies against the antigenic peptide portion of the fusion protein. Accordingly, neither the Peterhans nor the Handl assays are sandwich assays as is the competitive assay of the invention.

Antibodies against HTLV-III were measured in U.S. Pat. No. 4,774,175 to Chang, T. W. et al., using a fusion protein carrying determinants of the virus fixed onto a solid phase.

The above studies show that determination of markers in a clinical setting can be improved by providing an assay of higher sensitivity and/or specificity (above 95%). Such assay will increase clinical diagnosis accuracy by using markers specific for, e.g., different types of cancer and the endocrine system, among others, provided that the markers can be obtained with substantial purity to develop antibodies against them of high avidity and specificity.

DISCLOSURE OF THE INVENTION

This invention relates to an in vitro solid phase competitive assay for detecting the presence of an antigenic analyte or a functional fragment thereof in a biological test sample, comprising providing an antibody having specificity for an antigenic peptide, said antibody being bound to a solid support at a site other than the antigenic peptide binding site;

adding thereto a fusion protein of the antigenic peptide or a functional fragment thereof and an antigenic analyte or a functional fragment thereof, and allowing for the solid support-bound antibody to form a complex with the antigenic peptide portion of the fusion protein;

adding thereto a biological test sample suspected of comprising the analyte or a functional fragment thereof;

admixing thereto an anti-analyte antibody in stoichiometric proportion with respect to the fusion protein and allowing for the anti-analyte antibody to bind the free analyte or fragment thereof and the analyte portion of the solid support-bound fusion protein;

adding thereto a labeled antibody binding molecule and allowing for a labeled antibody binding molecule anti-analyte antibody-fusion protein-solid support-bound anti-antigenic peptide antibody complex and a free analyte or fragment thereof-anti-analyte antibody-antibody binding molecule complex to form; and determining the amount of solid support-bound label and comparing it with the amount of solid support-bound label in a similar assay conducted by substituted an equivalent volume of buffer for the test sample.

This invention also relates to an in vitro solid phase competitive assay method for detecting the presence of neoplastic tissue from a solid tumor or metastasis of a mammary organ of a mammal, comprising providing an antibody having specificity for an antigen peptide or a functional fragment thereof, said antibody being bound to a solid support at a site other than the antigenic peptide binding site;

adding thereto a fusion protein of the antigenic peptide or a functional fragment thereof and a surface antigen of a normal differentiated epithelial cell of a mammary organ of a mammal or a functional fragment thereof, and allowing for the solid support-bound antibody to form a complex with the antigenic peptide portion of the fusion protein;

adding thereto a serum test sample suspected of comprising neoplastic tissue from a solid tumor or metastasis of a mammary gland or a functional fragment thereof;

admixing thereto an antibody specific for a cellular antigen of normal mammary organ differentiated epithelial cells in stoichiometric proportion with respect to the fusion protein and allowing for the anti-epithelial cell antibody to bind the tissue antigen and the mammary cellular antigen portion of the solid phase-bound fusion protein;

adding thereto a labeled antibody binding molecule and allowing for a labeled antibody binding molecule-antimammary epithelial cell antigen antibody-fusion protein-solid support-bound anti-antigenic peptide antibody complex and a free neoplastic tissue-antiepithelial cell antigen antibody complex to form; and determining the amount of solid support-bound label and comparing it with the amount of solid support-bound label in a similar assay conducted by substituting an equivalent volume of buffer for the test sample.

Also provided herein is a fusion protein comprising a first antigenic polypeptide and a second antigenic polypeptide comprising an epitopic binding region of an antigen for a monoclonal antibody, the remainder of the second polypeptide being selected from the group consisting of the remainder sequence of the antigen and functional fragments or precursors thereof and an amino acid sequence which is partially or totally antigenically different from the antigen that binds the monoclonal antibody, the first antigenic polypeptide being antigenically different from the antigen and the second antigenic polypeptide.

Still part of this invention is a method of producing the above described fusion protein, comprising obtaining an antigen and a hybridoma encoding a monoclonal antibody against the antigen, selecting DNA fragments encoding polypeptide sequences that bind the antibody by screening a DNA library with the monoclonal antibody, cloning into an expression vector a DNA fragment comprising DNA sequences encoding the antigenic polypeptide and one of the selected DNA fragments, transfecting an expressing host with the DNA fragment carrying vector, selecting a vector carrying host expressing the fusion protein, culturing the host in an expression medium and isolating the fusion protein.

A more complete appreciation of the invention and many of the attendant advantages thereof will be readily perceived as the same becomes better understood by reference to the following detailed description.

BEST MODE FOR CARRYING OUT THE INVENTION

This invention arose from a desire by the inventors to improve on known technology for detecting the presence of antigenic analytes in a biological sample. The present assays provide higher sensitivity, and specificity, and greater ease than previously known assay procedures.

In the present assay, an antibody raised against an antigenic peptide is attached to a solid support. Thereafter, a fusion protein of the antigenic polypeptide and an antigenic analyte whose presence is suspected in a sample, is incubated with the solid support-bound antibody and a sample to be tested. This permits for the fusion protein and the antigenic analyte present in the sample to compete for available binding sites on the antibody against the anti-antigenic peptide and bind to it. Thereafter, an antibody raised against the antigenic analyte is added and allowed to bind to the analyte and the analyte portion of the fusion protein, and the presence of a double antibody-fusion protein sandwich bound to a solid support is determined. The latter step can be implemented by adding a labeled antibody detecting molecule such as gamma-globulin or a fragment of the immunoglobulin labeled with an enzyme, a fluorescent tag and/or a radioactive atom. Other antibody binding or detecting molecules may also be utilized such as protein A or protein G, fragments and precursors thereof, or single antibody chains, such as heavy chains.

The methodology demonstrated herein comprises a solid phase that is created on a substrate such as microtiter wells by methylated BSA to which an antibody having specificity for an antigen peptide or fragment thereof is bound, then adding to it a fusion protein produced by recombinant DNA carrying bacteria, where a segment of the fusion protein is a part or the whole of the antigenic peptide and another segment of the fusion protein is a part or the whole of a functional antigenic analyte; adding to the above a biological test sample containing part or the whole analyte and adding an anti-analyte antibody in stoichiometric proportion to the segment of the fusion protein that is part or the whole of the analyte; then adding a labeled antibody binding molecule such as an immunoglobulin with the purpose of detecting the amount of anti-analyte antibody that remains bound to the fusion protein. Optionally, the fusion protein is first separated from unbound anti-analyte antibody and unbound biological test sample.

This methodology offers, among others, the following advantages. The solid phase on the microtiter well is firmly attached. The antibody having specificity for the functional antigenic peptide fragments thereof is covalently bound to the solid phase, e.g., methylated BSA solid phase. The antibody binding the functional antigenic peptide or fragments thereof participates in purifying the fusion protein that includes the functional antigenic peptide or fragments thereof. The purified fusion protein also carries a purified analyte or fragment thereof that is then a key part of the assay and is thus purified under undenaturing conditions. The analyte or fragment thereof is conveniently bound by the antibody on the microtiter plate for the next steps of the assay. The fusion protein carrying the analyte or fragment thereof can be changed together with the anti-analyte antibody. The rest of the assay components remain unchanged. Thus, different analytes can be tested in relation to a certain clinical condition. The fusion protein carrying the analyte or fragment thereof can be produced in inexhaustible amounts. The anti-analyte antibody in the form of a hybridoma product (monoclonal antibody) can be prepared in inexhaustible amounts as well.

The method of detection using conjugate antibody binding molecules could have different types of conjugates to fit desired signal for the assay.

The present methods may be applied to the detection of different antigens in body fluids, biological fluids, neoplastic or cancerous tissues, various tissue and cancer markers, and other antigenic agents which might be present in a biological sample. When a neoplastic marker is found, the results may be compared with those of similar normal tissue. The assays described herein may also be utilized for determining the origin of the tissue for such neoplastic markers. Mammalian blood or serum may be monitored for the presence of normal cellular antigens specific for differentiated cells obtained from patients suspected of having a cancer of a particular cell type. Receptors, e.g., antibodies, specific for plurality of determinant sites associated with normal cellular antigens may be utilized for composing the fusion protein (as the antigenic analyte therein).

The present assays may be applied to the measurement of levels of a specific antigenic analyte in a host's tissue suspected of having a solid primary tumor and/or metastasis thereof by comparing the results of the assay to a similar assay conducted on a sample reflecting normal levels of similar antigens in blood.

The subject invention provides a method for determining the presence of solid tumors and/or metastases in a mammalian host, indicating not only the presence or absence of neoplastic tissue but also the nature or source of the neoplastic tissue. Various mammalian hosts may be diagnosed, such as research animals, domestic animals, pets and humans. A serum sample is employed and the presence of an elevated concentration of normal cellular or cancer associated antigen from non-circulating normal tissue is determined. That is, the cellular antigens can be specific for a number of different structural organs. The organs of interest may be encased in a facium membrane. The cellular antigens and other antigenic materials which may be associated with the differentiated cell may then be monitored.

Illustrative organs of interest include the breast, prostate, colon, bladder, heart, kidney, lung, brain, muscle, nerves, etc.

The concentration level of at least one cellular antigen analyte in serum is determined and may be compared to the normal level of such cellular antigen. The cellular antigen may be free of other materials, may be a fragment of a surface antigen or may be part of a cell membrane associated with other cellular antigens. Particularly, the cellular antigen may be a normal antigen associated with a differentiated cell, usually a mature cell. The presence of the cellular antigen may be detected by receptors specific for one or more determinant sites. For example, the sites may be exposed while the antigen extends into the membrane or may become exposed when the surface antigen is freed from the membrane. Other sites may not be membrane bound. Under some circumstances, it may be desirable to detect only one determinant site. Under other circumstances two or more determinant sites, particularly determinant sites on different cellular antigens specific for the differentiated cell, may be available. In such cases it may be desirable, and even more preferable, to detect two or more determinant sites on each of two or more cellular antigens specific for the differentiated cell of interest. By demonstrating that two or more antigens specific for the differentiated cell of interest have elevated concentrations in the circulation, greater confidence in the existence of neoplastic tissue can be achieved as well as a better recognition of the type of tissue of origin that releases the antigen.

While any receptor or anti-antigen analyte antibody may be employed which is specific for the determinant site(s) of interest, for the most part the receptors will be antibodies, either polyclonal or monoclonal. In addition, while any immunoglobulin may be employed, for the most part IgG will be employed, either whole antibodies or fragments thereof, e.g., $F(ab')_2$, Fab, Fd, F or heavy or light chains thereof. As indicated, while single monoclonal antibodies may be employed, sometimes mixtures of antibodies will be employed, including mixtures of monoclonal antibodies or mixtures of polyclonal antibodies. The number and type of antibodies which are employed will depend upon the number of determinant site(s) and number of different cellular antigens which are to be measured. The antibody composition may be free of antibodies specific for antigens other than the specified cellular antigenic analyte.

The differentiation cellular antigenic analyte can be detected by preparing antibodies against antigens in the cell, cell membrane, or other cellular antigens of interest, and then screening against a number of different cells from other tissue. Particularly, one can screen the antibodies by combining them with cellular antigens or cell membranes from a variety of cells different from the cell of interest, particularly where the cellular antigens and cells are bound to a support allowing for ready separation between antibodies which do not bind and antibodies which do bind. The antibodies may then be purified by combination with cellular antigens from the cell of interest which are bound to a support, and further release of the antibodies with various solutions, such as sodium isocyanate or acetic acid, at a concentration sufficient to break down the antigen-antibody complex.

The present assays are competitive protein binding assays which are in general classified as heterogeneous, and may involve a separation step between free label and label bound to the double antibody-fusion protein complex bound to the solid support. In the present assay, the support may be a particle such as a beads, a container's surface such as the wall of a microtiter plate well, a tube, a chromatographic plate and the like. Other substrates providing binding surfaces to which antibodies can bind, some of which are commercially available, can also be employed. The antigenic analyte contained in a sample is allowed to compete with the fusion protein bound to the anti-antigenic peptide antibody in the presence of an anti-antigenic analyte (antigen) antibody or fragment thereof. One of many labels may then be attached to the latter selected from radionucleides, enzymes, florescent molecules and the like. These are known in the art and need not be repeated herein.

The substrate to which the anti-antigenic peptide antibody is bound may be any one known in the art. Preferred, however, is the one described in U.S. Pat. No. 4,572,901 to Ceriani et al, the entire contents of which is incorporated herein by reference in order to enable the many details of the preparation of the substrate. Briefly, a proteinaceous composition is employed for modifying the binding characteristics of an article of manufacture which is capable of binding an antibody at a site other than its antigenic binding site.

The preparation of anti-antigenic analyte antibodies and anti-antigenic polypeptide antibodies is known in the art and need not be described herein in detail. By means of example, the methods disclosed in U.S. Pat. Nos. 4,229,426; 4,584, 268 and 4,486,530 and in Peterhans et al, supra, and Handl et al supra, may be utilized. For the development of monoclonal antibodies standard procedures may be utilized as generally described by Kohler and Milstein (Kohler and Milstein, Nature 256:495–497(1975)).

The preparation of labeled anti-antibody immunoglobulin or similar antibody-binding molecules is also known in the art and need not be further described herein. By means of example, methods such as those described in U.S. Pat. Nos. 4,229,426; 4,486,530 and 4,632,901 can be utilized. The entire contents of these patents is incorporated herein by reference.

The preparation of the fusion protein of the antigenic analyte and an antigenic peptide is also known in the art and need not be fully described herein. By means of example, the techniques illustrated by Handl et al, supra, Peterhans et al, supra and, U.S. Pat. No. 4,745,055 may be utilized. The entire contents of these references are incorporated herein by reference for enablement purposes.

It is therefore provided herein an in vitro solid phase competitive assay for detecting the presence of an antigenic analyte or a functional fragment thereof in a biological test sample, comprising providing an antibody having specificity for an antigenic peptide, said antibody being bound to a solid support at a site other than the antigenic peptide binding site;

adding thereto a fusion protein of the antigenic peptide or a functional fragment thereof and an antigenic analyte or a functional fragment thereof, and allowing for the solid support-bound antibody to form a complex with the antigenic peptide portion of the fusion protein;

adding thereto a biological test sample suspected of comprising the analyte or a functional fragment thereof;

admixing thereto an anti-analyte antibody in stoichiometric proportion with respect to the fusion protein and allowing for the anti-analyte antibody to bind the free analyte or fragment thereof and the analyte portion of the solid support-bound fusion protein;

adding thereto a labeled antibody binding molecule and allowing for a labeled antibody binding molecule anti-analyte antibody-fusion protein-solid support-bound anti-antigenic peptide antibody complex and a free analyte or fragment thereof anti-analyte antibody-antibody binding molecule complex to form; and determining the amount of solid support-bound label and comparing it with the amount of solid support-bound label in a similar assay conducted by substituting an equivalent volume of buffer for the test sample.

Preferred conditions for the practice of this invention are as follows. However, a skilled practitioner would know how to adapt the collective knowledge of the art for the practice of the present method as applied to different antigenic peptides and antigenic analytes.

The method may be also applied to fields other than cancer. Examples of other applications are, e.g., measuring levels of hormones and other molecules in biological samples, veterinary medicine, food and other industries, agriculture, various research fields, quality control and any other field in which immunoassays are employed.

The antigenic peptide may be any polypeptide or a fragment thereof capable of eliciting an immunoglobulin response in a mammal. Examples thereof are β-galactosidase, chloramphenicol acetyltransferase, CII gene product of lambda phage, $E.$ $coli$ trpE gene product, alkaline phosphatase, human growth hormone or antigenic fragments or precursors thereof. However, any other antigenic peptide or active fragment or precursor thereof may also be utilized.

The antibodies raised against the antigenic peptide or active fragment thereof may be a polyclonal or monoclonal antibody and it may be bound to the solid support by methods known in the art such as the method described in U.S. Pat. No. 4,572,901. However, other methods may also be utilized. The anti-antigenic peptide antibody must be bound to the solid support at a site other than its antigenic peptide binding site in order that the solid support may not interfere with the reaction of the antibody with the antigenic peptide when practicing the method of the invention.

The solid-support bound antibody may be provided in solution and/or suspension at a concentration of about 0.0001 to 100 mg/ml, and more preferably about 0.0001 to 0.05 mg/ml of solution or suspension. In addition, the solution or suspension may also contain, e.g., a buffer, phosphate buffered saline+0.3% Triton X100, Tris buffered saline, and detergents, among others. The pH of the solution suspension is preferably maintained at about 6.0 to 8.0, and more preferably at about 6.80 to 7.8.

The biological sample suspected of containing an antigenic analyte may be diluted and/or otherwise treated as is known in the art. By means of example, the sample may be treated as described in U.S. Pat. Nos. 4,584,268; 4,486,530 and 4,433,059. However, other treatments are also contemplated within the context of this invention which are generally known in the art.

The fusion protein or functional fragment thereof is added to the solid support-bound anti-antigenic peptide antibody in a ratio of preferably of about 1:2,000 to 2,000:1 wt:wt, and more preferably about 1:20 to 20:1 wt:wt and allowed to incubate under conditions and for a period of time effective to form a complex between the support-bound antibody and the antigenic peptide portion of the fusion protein. Typically, the complex is allowed to form at a temperature of about 4° to 40° C., and more preferably at about 18° to 30° C. at a pH of about 6.0 to 8.0, and more preferably at about 6.8 to 7.8.

The biological test sample is treated and/or diluted so that it contains about 0.00001 to 300 mg/ml of protein, and more preferably about 0.001 to 80 mg/ml of protein. A volume of the biological sample containing about 0.0001 to 16 mg of protein, and more preferably about 0.01 to 12 mg of protein, is added to the reaction mixture already containing the above-described complex under conditions effective to promote the competition between the analyte suspected of being comprised in the biological sample and the antigenic analyte portion of the fusion protein for the subsequently-added anti-analyte antibody.

Stoichiometric amounts of anti-analyte antibody to analyte or fragment thereof constituting the fusion protein may be added in a given volume at a concentration of about 0.00001 to 0.06 mg/ml solution, and more preferably about 0.0003 to 0.003 mg/ml solution in phosphate buffered saline plug 0.01 to 5% bovine serum albumin at pH about 6 to 8, and more preferable about 6.8 to 7.2

The anti-analyte antibody is added in about stoichiometric proportions with respect to the fusion protein present in the reaction mixture and allowed to bind the analyte portion thereof and any free analyte present in the biological sample. Preferred conditions for this step are about 4° to 40° C., more preferably about 15° to 30° C., and a pH of about 6 to 8, more preferably about 6.8 to 7.2. The incubation may be conducted for about 1 to 48 hours, and more preferably about 10 to 18 hours, and optionally with agitation.

A labeled antibody binding molecule such as anti-antibody immunoglobulin or active fragment thereof, protein A or G or active fragments thereof having affinity for an antibody is then added under conditions effective for the formation of a labeled antibody binding molecule/anti-analyte antibody fusion protein/anti-antigenic peptide antibody complex and a free analyte or fragment thereof/anti-analyte antibody/antibody binding molecule complex. The conditions may be about 4° to 40° C., and more preferably about 15° to 30° C. and a pH of about 6.0 to 8.0, and more preferably about 6.8 to 7.8.

The antibody binding molecule is prepared by methods known in the art (e.g., Goding, T., Immunological Methods 20:241(1978) for protein A, Bjork and Kronvall J., Immunology 133:969(1984) for protein G, and U.S. Pat. Nos. 4,229,426: 4,584,268 and 4,486,530).

The antibody binding molecule may carry a label such as an enzyme, a fluorescent tag or a radionucleide. Suitable labels for each category are known in the art as are the methods for attaching them to the antibody binding molecules and determine the amount of label present. The following the attaching such labels are provided solely by means of example. (The and Feltkamp, Immunology 18:865–873(1970) for enzyme-linked assays, Avrameas, Immunochemistry 6:43–52(1969) for fluorescent tagging, and for radiolabeling, Greenwood et al, Biochemical J. 89:114–123(1963)).

The determination of the amount of solid support-bound label may be conducted by methods known in the art which need not be described herein in detail. The amount of radionucleide may be determined by liquid scintillation, radioactivity counting, thin layer chromatography and other known methods. The determination of an enzyme may be conducted by adding to the solid support-bound label an amount of enzyme substrate and measuring the amount of the substrate converted to product or any other variable representative of the amount of enzyme present. Similarly, the amount of florescent labeled present can be determined by measuring the amount of florescent light at a specified wave length.

The method requires the determination of the amount of solid support-bound label in the presence and absence of the biological sample. This is for comparative purposes, where the results obtained in the absence of the biological sample are taken as control and this value substracted from the value obtained when the method is conducted in the presence of the sample.

In a particularly preferred embodiment of the invention, the anti-antigenic peptide antibody is a monoclonal antibody. In another preferred embodiment of the invention, the anti-analyte antibody is a monoclonal antibody. And, in still another preferred embodiment of the invention, the solid support is coated with a ($C_1$–$C_3$) alkylated poly(amino acid) of at least about 30,000 Dalton molecular weight that is insoluble in water at 25° C. and soluble to at least 0.01 wt. % in an aqueous solution of at least about 0.005 wt. % in an aqueous solution of at least about 0.005 wt. % of a non-ionic detergent; and the anti-antigenic polypeptide antibody is bound to the poly(amino acid) via glutaraldehyde bridges.

In another preferred embodiment of the method, the antigenic analyte comprises a tissue marker such as a cellular differentiation cell antigen or a marker for malignant cells. Examples are breast epithelial antigens, carcinoembryonic antigens, prostatic antigens, growth hormone and serum albumin, among others. However, any other antigenic cell marker may be utilized for the practice of the invention. The analyte may be a malignant cell marker or antigenic fragment thereof as well.

In one aspect of the assay, the solid phase-bound complex is further separated from the remainder of the assay components before adding the anti-analyte antibody and the biological sample and the labeled antibody binding molecule and before the determining step.

In a preferred embodiment, the antibody binding molecule such as immunologlobulins, protein A, protein G or active fragments or precursors thereof are radiolabeled.

In another preferred embodiment, the antibody binding molecule such as immunoglobulin, protein A, protein G, or active fragments or precursors thereof are enzyme labeled and the determining step is conducted by first adding a substrate for the enzyme and then determining the amount of substrate converted to product by the solid support-bound enzyme and comparing this value to the amount of substrate converted to product in a similar assay conducted in the absence of the biological sample.

In a further preferred embodiment of the assay, the free labeled antibody binding molecule-antibody-free analyte complex is separated from the solid-support bound labeled complex.

In another aspect of this invention, it is provided an in vitro solid phase competitive assay method for detecting the presence of neoplastic tissue from a solid tumor or metastasis of a mammary organ of a mammal, comprising providing an antibody having specificity for an antigen peptide or a functional fragment thereof, said antibody being bound to a solid support at a site other than the antigenic peptide binding site;

adding thereto a fusion protein of the antigenic peptide or a functional fragment thereof and a cellular antigen of a normal epithelial cell of a mammalian mammary organ or a functional fragment thereof, and allowing for the solid support-bound antibody to form a complex with the antigenic peptide portion of the fusion protein;

adding thereto a serum test sample suspected of comprising neoplastic tissue from a solid tumor or metastasis of a mammary organ or a functional fragment thereof;

admixing thereto an antibody specific for a cellular antigen of normal mammary epithelial cells in stoichiometric proportion with respect to the fusion protein and allowing for the anti-epithelial cell antibody to bind the neoplastic tissue and the mammary cellular antigen portion of the solid phase-bound fusion protein;

adding thereto a labeled antibody binding molecule and allowing for a labeled antibody binding molecule-anti mammary epithelial cell antigen antibody-fusion protein-solid support-bound anti-antigenic peptide antibody complex and a free neoplastic tissue-antiepithelial cell antigen antibody complex to form; and determining the amount of solid support-bound label and comparing it with the amount of solid support-bound label in a similar assay conducted by substituting an equivalent volume of buffer for the test sample.

In general, the ingredients and the conditions for conducting the various steps of this assay are similar to those described above.

There will be a variety of situations where the serum of a host will be measured for detection of the presence of neoplastic tissue. In population screening and original diagnosis, where a host is suspected of having a neoplasm, the serum may be screened for cellular antigens of a particular tissue which is suspected of having developed a neoplasm. This test can be used in conjunction with other tests, to enhance the confidence level of the presence of a carcinoma. Where a carcinoma has been detected and removed, the presence of residual neoplastic tissue or metastases may be determined. In addition, where a mass is found suggestive of a metastasis of unknown origin, the origin can be determined by employing antibodies specific for different types of tissue. Furthermore, the clinical applications include the detection of residual tumor masses (local or metastic) after therapy and in the follow-up for recurrence after the neoplastic tissue has been eradicated.

The labeled antibodies may be supplied as a lyophilized powder or in a solution that can be kept at a temperature from about below freezing to 40° C. in combination with conventional stabilizers and other additives including buffers, neutral salts, bulking agents, inert proteins, detergents such as non-ionic detergents, and other additives associated with the nature of the label, such as substrates for the enzyme label. These additives will be present in varying amounts. The following are preferred amounts. The antibodies may be present at about 0.005 to 5 wt %, preservatives at about 0.001 to 1 wt %, neutral salts at about 0 to 15 wt %, protein at about 0 to 10 wt % and the remainder bulking agent. The labeled antibody may be combined with various excipients, which may serve as extenders and aid in handling and stabilization of the labeled antibody.

Usually, the labeled antibodies will be provided as a kit in combination with controls to produce a standard curve. The controls will have the antigen molecule usually formulated with minor amounts of additives such as inert protein, non-ionic detergents, e.g. Triton X-100 buffer, preservatives or the like. Also included will be bulking agents, e.g., mannitol. The minor additives will range from about 0.001 to 2 wt %. The antigen will be present in varying amounts to provide the desired concentration on dissolution into a prescribed volume.

The reagent antibody suspensions or solutions may contain in addition an additive such as a buffer, e.g., phosphate, Tris, barbital or the like, normally in concentrations of about 0.01 to 1 mM, and more preferably 0.05 to 0.1 mM, the concentration being effective to provide a preferred pH of about 6.5 to 9, and more preferably about 7 to 8, during the assay. Other additives which may be utilized are preservatives such as sodium azide, inert proteins such as serum albumin, sodium chloride, detergents and the like. These additives serve to preserve the protein components of the reagents, enhance the formation of antigen-antibody complexes, prevent non-specific binding, and the like.

The present methods permit the detection of at least about 1 mg/ml to 10 mg/ml of analyte, and in some instances lower than about 1 mg/ml and even greater than about 10 mg/ml.

Also part of this invention is a kit for detecting the presence of an antigenic analyte, comprising a fusion protein of about 50 to 1,200 amino acids comprising an antigenic analyte or binding active fragment thereof of about 30 to 600 amino acids and an antigenic peptide or binding active fragment thereof of about 7 to 600 amino acids, the antigenic peptide being antigenically different from the analyte;

a first antibody or binding active fragment thereof having affinity and specificity for the antigenic analyte, binding active fragment thereof or binding active precursor thereof;

a second antibody or binding active fragment thereof having affinity and specificity for the antigenic peptide or binding active fragment thereof, the second antibody being bound at a site other than the binding site for the antigenic peptide; and an antibody binding molecule.

The fusion protein is as described above comprised of an antigenic analyte or a binding active fragment thereof and an antigenic peptide or binding active fragment thereof which is antigenically different from the analyte. The first antibody or binding active fragment thereof is also as defined above and has affinity and specificity for the antigenic analyte or binding active fragment thereof. The second antibody or binding active fragment thereof was also described above and has affinity and specificity for the antigenic peptide or a binding active fragment thereof. The second antibody as indicated above is bound to a solid support at a site which is different from the binding site for the antigenic peptide in the antibody molecule. All the components for the kit have been described in the text of this patent as have been methods for preparing them.

In a preferred embodiment of the invention the analyte is selected from the group consisting of HMFG differentiation antigens of about 70, 45–48, 150 and 400 Kdalton molecular weights, binding active fragments or precursors thereof and binding active precursors thereof.

In another preferred embodiment of the invention the antigenic peptide is β-galactosidase or an antigenic fragment thereof.

In still another preferred embodiment the first antibody raised against the antigenic analyte or binding active fragment thereof comprises a monoclonal antibody or a binding active fragment thereof.

In still another preferred embodiment the second antibody raised against the antigenic peptide or a binding active fragment thereof comprises a monoclonal antibody or binding active fragment thereof.

In still another preferred embodiment the first antibody raised against the antigenic analyte or binding active fragment thereof comprises a polyclonal antibody or a binding active fragment thereof.

In still another preferred embodiment the second antibody raised against the antigenic peptide or a binding active fragment thereof comprises a polyclonal antibody or binding active fragment thereof.

In still another preferred embodiment of the kit of the invention the solid support is coated with a ($C_1$–$C_3$) alkylated poly(amino acid) of at least about 30,000 Dalton molecular weight that is insoluble in water at 25° C. and soluble to at least 0.01 wt % in an aqueous solution of at least about 0.005 wt % of a non-ionic detergent, and the anti-antigenic polypeptide antibody is bound to the poly(amino acid) via glutaraldehyde bridges.

In another variation of the kit the antibody-binding molecule is selected from the group consisting of anti-globulins, protein A, protein G and antibody binding active fragments and precursors thereof.

Still part of this invention is a fusion protein, comprising a first antigenic polypeptide; and a second antigenic polypeptide comprising an epitopic binding region of an antigen for a monoclonal antibody, the remainder of the second polypeptide being selected from the group consisting of the remainder sequence of the antigen and functional fragments or precursors thereof and an amino acid sequence which is partially or totally antigenically different from the antigen that binds the monoclonal antibody, the first polypeptide being antigenically different from the antigen and the second antigenic polypeptide.

In a particularly preferred embodiment the fusion protein comprises the sequence AspLeuArgProglyPro or HisThrArgProAlaPro. In a still more preferred embodiment the fusion protein comprises MP5 or MP4 or fragments thereof.

Also provided herein is a method of producing the fusion protein described above, comprising obtaining an antigen and a hybridoma expressing a monoclonal antibody against the antigen;

selecting DNA fragments encoding polypeptide sequences that bind the antibody by screening a DNA library with the monoclonal antibody;

cloning into an expression vector a DNA fragment comprising DNA sequences encoding the first antigenic polypeptide and one of the selected DNA fragments;

transfecting an expressing host with the DNA fragment carrying vector;

selecting a vector carrying host expressing the fusion protein;

culturing the host in an expression medium; and isolating the fusion protein.

Techniques suitable for conducting every step of the above method are known in the art and need not be detailed herein (Sambrooke, et al, Molecular Cloning: A Laboratory Manual, Cold Spring Harbor) (1989); Stanley, K. K. and Luzio, I. P., EMBO J.3:1492–1434(1984)).

Examples 6 and 7 provided below disclose the fusion proteins NP5 and NP4 and illustrate a general method for producing fusion proteins that contain a first antigenic polypeptide and at least one epitope for a single monoclonal antibody among a group of monoclonal antibodies raised against he same antigen or against the same natural polypeptide. This method is especially useful when the group of monoclonal antibodies bind to a restricted region of an antigen and it is desired to obtain an antigenic polypeptide (the second polypeptide referred to above) that binds to only one of the monoclonal antibodies. The thus constructed fusion protein is particularly useful for incorporation into a kit and/or immunoassay.

The method encompasses the screening of a cDNA or genomic expression library with a monoclonal antibody and the selection of plaques that bind the antibody with methods known in the art. Even if the DNA gernomic library contains the sequence of the, e.g., natural polypeptide antigen to which the monoclonal antibody binds, there is only a 1 in 6 probability that the inserted DNAs will encode the natural polypeptide sequence given that 3 nucleotides are necessary to encode each amino acid and that there are 2 strands of DNA being constructed. There is therefore a ⅚ probability that the polypeptide antigen portion of the fusion protein encoded by the DNA inset is other than the naturally produced or antigenic epitope sequence used to raise the antibody.

These non-natural polypeptide portions of the fusion protein bind the monoclonal antibody used to select them through an amino acid region resembling the natural epitope. The rest of the polypeptide sequence is, however, antigenically different from the original antigen sequence.

The non-natural sequence containing fusion protein may be used in kits and immunoassays having greater specificity and sensitivity than assays using a fusion protein of the native antigen. Such is the case for the immunoassay discussed in example 4 below using the NP5 fusion protein and the Mc5 monoclonal antibody.

The cDNA library may be constructed with cDNA from a tissue or cell that produces a native antigen identified by the monoclonal antibody used for screening. Alternatively, it may be constructed with cDNA from a tissue or cell that does not produce that native antigen. Furthermore, the library may also be constructed with genomic DNA, since it is feasible to screen several million phage plaques with any one monoclonal antibody.

The examples, e.g., Example 4 utilizing NP5 and the accompanying discussion illustrate that non-naturally occurring polypeptides and polypeptides solely sharing one epitope with an antigen may be synthesized as fusion proteins that contain antibody binding regions that resemble the natural epitope, with the rest of the polypeptide being different from that of the original antigen polypeptide against which the antibody was made.

The second antigenic polypeptide may comprise sequences of naturally occurring as well as synthetic antigens. In a particularly preferred embodiment the second antigenic polypeptide comprises an epitopic binding region of an antigen for a monoclonal antibody, the remainder of the second polypeptide being selected from the group consisting of the remainder sequence of the antigen and functional fragments or precursors thereof and an amino acid sequence which is partially or totally antigenically different from the antigen that binds the monoclonal antibody, and the first antigenic polypeptide having at least one antigenically different epitope from the antigen and the second antigenic polypeptide.

In order to comply with the best mode requirement, the Mc5 hybridoma cell line expressing the Mc5 monoclonal antibody has been deposited with Bernard Lasher, MD, PhD., Laboratory Director, John Muir Memorial Center, 1601 Ignacio Valley Road, Walnut Creek, Cal. 94598. The cell line will be deposited with the ATCC in Rockville, Md. before issuance of a patent.

Having generally described this invention, the same will be better understood by reference to certain specific examples, which are included herein for purposes of illustration only and are not intended to be limiting of the invention or any embodiment thereof, unless so specified.

EXAMPLES

Example 1: Preparation of Methylated BSA Attached to Solid Phase Support

The methylated BSA for the solid phase in the microtiter plastic wells was prepared, used and covalently bound to the antibody having specificity for an antigenic peptide or fragment thereof as described in U.S. Pat. No. 4,572,901 to Ceriani et al.

Example 2: Preparation of Polyclonal anti-β-galactosidase Antibody

The antibody having specificity for an antigenic peptide or fragment thereof was prepared by injecting the antigenic peptide (β-galactosidase, SIGMA) to rabbits and absorption with *E. coli* strain Y1090 extracts under conditions where the microorganism does not express β-galactosidase.

Example 3: Preparation of Fusion Protein

The fusion protein was created by infecting *E. coli,* strain Y1090, with a phage population part of a cDNA library created from human breast cancer cell MCF-7, in accordance with Sambrooke et al, supra.

Bacterial phage expressing the analyte or fragments thereof as detected by monoclonal antibody Mc5 were isolated. The DNA of a lambda-phage carrying genetic information for an analyte or fragments thereof detected by Mc5 was separated by poly(ethylene glycol) precipitation, cut with restriction enzymes, and the appropriate DNA fragment carrying sequences for the analyte or fragments thereof was inserted into the circular plasmid DNA pEX2 (Stanley and Luzio, supra) at the EcoR1 restriction enzyme recognition site downstream from the lac gene.

Under appropriate conditions these bacteria carrying the information for the analyte or fragments thereof produced fusion proteins comprising β-galactosidase (or fragments thereof) and the analyte (or fragments thereof). The fusion protein was concentrated in inclusion bodies in the *E. coli* bacteria. Thereafter, the inclusion bodies were separated and the fusion protein carried therein was purified as described in Example 5.

Example 4: Assay Protocol

The assays were set up as follows.

i) 50 ug of methylated BSA were dissolved in PBS+0.3% Triton X100÷0.5% sodium azide and bound to microtiter plates per well by incubation and drying overnight at 37° C. (as described in U.S. Pat. No. 4,572,901). 50 μl of buffered 0.25% glutaraldehyde were then placed in each well for 1 hr, to be followed by 50 μl of a solution containing 2 μg/ml of anti-β-galactosidase antibody. 200 μl of 0.5 mM glycine solution in PBS were added for 1 hr to block any not completely cross-linked glutaraldehyde.

ii) 0.01 to 1.0 μg of the purified fraction containing the NP5 fusion protein dissolved in a buffer solution were added per well and let stand for 1 to 16 hrs.

iii) 30 μl of a solution containing 0.1 to 1.0 μg/ml of Mc5 monoclonal antibody (in a stoichiometric amount to the fusion protein added) were added together with 20 μl of a 1:6 dilution of patient serum in 1–30% human female serum in PBS. The Mc5 monoclonal antibody binds the about 400 Kdalton breast epithelial mucin. The mixture is let stand overnight at room temperature.

iv) The next day the monoclonal antibody was washed with PBS. Thereafter, the amount of monoclonal antibody bound to the solid phase was detected with $^{125}$I-labeled goat anti-mouse IgG by adding 200,000 to 2,000,000 cpm of the labeled immunoglobulin. The mixture allowed to stand for 1–6 hrs, the well was then washed and the amount of label counted.

v) The amount of $^{125}$I-labeled goat anti-mouse IgG bound was compared to a standard curve constructed by adding to the assay mixture increasing amounts of human milk fat globule (HMFG) diluted in 1–30% human female serum in PBS instead of patient serum.

Example 5: Preparation of Fusion Protein from Bacterial Culture 1 ml of 100 mg/ml ampicillin was added to 1000 ml of LB medium and mixed. 50 ml of inoculant culture were then added to 1000 ml of LB medium (1:20 ratio). This culture was maintained at 28°–30° C. in a shaker incubator until an O.D.600 nm=0.5 was obtained as compared to LB medium taken as blank (approximately 4 hrs). The culture was transferred to a 42° C. shaker water bath for 1 hr. and then brought back to 37° C. and incubated for 1 hr. The culture flasks were taken out and kept on ice. The contents thereof were transferred to centrifuge tubes and the tubes centrifuged at 4,500 r.p.m. for 15 minutes at 4° C. in a Sorvall GSA rotor. The supernatant was thrown away after bleach addition. The pellets were weighed and lysozyme (0.8 mg/gm cells) in lysis buffer added thereto.

The suspensions were thoroughly mixed by drawing liquid up and down a pipet a number of times (Increasing viscosity signals lysis). Deoxycholate (Na salt, 4 mg/gm of cells) in lysis buffer was then added and mixed again using a pipet. The viscosity of the solution as maximal at this state. Each tube was then sonicated three times for 30 sec (30 sec. on and 30 sec. off with minimum suds formation). This solution was then centrifuged for 15-minutes at 12,000 g at 4° C. The supernate was then separated. The pellet was weighed and 9 times the volume (v/w) of lysis buffer (10 mM EDTA and 0.5% Triton X-100) was then added and mixed using a pipet. The last two steps were repeated twice and supernates II and III respectively were marked as such. The pellet was weighed and dissolved in 68 mM Tris+ 2%SDS+2% β-mercaptoethanol (approximately 1 gm in 90 ml) using a pipet. A 1 mM concentration of phenylmethylsulfonyl fluoride (PMSF) was then added. When the solution was completely clear, it was dialyzed against 1×PBS+0.3% Triton X-100 at room temperature.

The dialyzed preparation was run on a 7.5% stacked gel along with supernates I, II & III. A Western blot was performed to detect any protein degradation occurring during dialysis (Towbin, T. H., et al, PNAS 76:4350(1979)). The total protein concentration was estimated by the Bradford method (Bradford, M., Anal.Biochem.72:248(1976)).

Lysis buffer
50 mM Tris, PH=8.0 (Tris HCl)
1 mM EDTA
100 mM NaCl

LB Media
Bacto-Tryptone—10 gm
Bacto-Yeast extract—5 gm
NaCl—10 gm
1M Tris (pH=7.5)—10 ml
pH to 7.5 using NaOH if necessary.
All in 1 liter of distilled water.

Example 6: Characteristics of NP5 cDNA Insert and Fusion Protein Encoded Therein The NP5 cDNA insert was isolated from a lambda/gt11 cDNA library created from the human breast cancer cell line MCF7 (Maniatis et al., supra) by screening with a monoclonal antibody mixture of Mc5, BrE1, BrE2 and BrE3 monoclonal antibodies. The fusion protein produced by bacteria infected with lambda/gt11 containing the NP5 insert bound only the Mc5 antibody. The NP5 cDNA was transferred to the PEX2 plasmid and the β-galactosidase fusion protein was then produced by the method described in Example 3, above.

The NP5 cDNA was subcloned into pGEM3 according to standard methods (Sambrook, et al, Molecular Cloning: A Laboratory Manual, Second Edition, Cold Spring Harbor Press, New York (1989)), and sequenced by the dideoxy method using a modified T7 DNA polymerase (sequenase) directly on the plasmid DNA using T7 or SP6 promoter sequence primers (Promega Biotec) according to the manufacturer's protocol (USB).

The DNA sequence of the coding strand was compared to sequences in GENBANK (FASTA: Intelligenetics Suite) and found to be homologous to that of human SP2 mRNA induced by estrogen (Jakowlew et al, Nucleic Acids Research 12:2861–2878(1984)). The DNA sequences are shown in Table 1, below.

TABLE 1

Comparison of DNA Sequence Homology Between NP5 DNA and SP2

| | | |
|---|---|---|
| NP5SP62001 | 5- | CGCCTTTGGAGCAGAGAGGAGGCAATGGCCACCATGGAGAACAAGGTGAT |
| HSPS2 | 17- | CGCCUUUGGAGCAGAGAGGAGGCAAUGGCCACCAUGGAGAACAAGGUGAU |
| NP5SP62001 | 55- | CTGCGCCCTGGTCCTGGTGTCCATGCTGGCCCTCGGCACCCTGGCCGAGG |
| HSPS2 | 67- | CUGCGCCCUGGUCCUGGUGUCCAUGCUGGCCCUCGGCACCCUGGCCGAGG |
| NP5SP62001 | 105- | CCCAGACAGAGACGTGTACAGTGGCCCCCCGTGAAAGACAGAATTGTGGT |
| HSPS2 | 117- | CCCAGACAGAGACGUGUACAGUGGCCCCCCGUGAAAGACAGAAUUGUGGU |
| NP5SP62001 | 155- | TTTCCTGGTGTCACGCCCTCCCAGTGTGCAAATAAGGGCTGCTGTTTCGA |
| HSPS2 | 167- | UUUCCUGGUGUCACGCCCUCCCAGUGUGCAAAUAAGGGCUGCUGUUUCGA |
| NP5SP62001 | 205- | CGACACCGTTCGTGGGGTCCCCTGGTGCTTCTATCCTAATACCATCGACG |

TABLE 1-continued

Comparison of DNA Sequence Homology Between NP5 DNA and SP2

| | |
|---|---|
| HSPS2 | 217- CGACACCGUUCGUGGGGUCCCCUGGUGCUUCUAUCCUAAUACCAUCGACG |
| NP5SP62001 | 255- TCCCTCCAGAAGTGTCTAAGGAATT |
| HSPS2 | 267- UCCCUCCAGAAGAGGAGUGUGAAUU |

268 bases of a 275 nucleotide overlap are identical (97.5%)

The amino acid sequence of the NP5 portion of the fusion protein that bound the Mc5 monoclonal antibody was compared to known sequences in the Swiss-pro database (PFSTSCN: PCGENE) and no extended homology was found to any known polypeptide.

The amino acid sequence of the NP5 portion of the fusion protein that bound the monoclonal antibody Mc5 was compared to known sequences in Swiss-pro database (PFSTSCN: PCGENE) and no extended homology was found. Sequences compared are shown in Table 2 below.

TABLE 2

Comparison of amino acid sequences of NP5 and SP2

```
             10        20        30        40        50        60
             |         |         |         |         |         |
NP5 cDNA   TTCCCGCCTTTGGAGCAGAGAGGAGGCAATGGCCACCATGGAGAACAAGGTGATCTGCGC

NP5 a.a.   PheProProLeuGluGlnArgGlyGlyAsnGlyHisHisGlyGluGlnGlyAspLeuArg
SP2 a.a.                           METAlaThrMETGluAsnLysValIleCysAla 70        80        90       100       110       120
             |         |         |         |         |         |
           CCTGGTCCTGGTGTCCATGCTGGCCCTCGGCACCCTGGCCGAGGCCCAGACAGAGACGTG

ProGlyProGlyValHisAlaGlyProArgHisProGlyArgGlyProAspArgAspVal
           LeuValLeuValSerMETLeuAlaLeuGlyThrLeuAlaGluAlaGlnThrGluThrCys 130       140       150       160       170       180
             |         |         |         |         |         |
           TACAGTGGCCCCCCGTGAAAGACAGAATTGTGGTTTTCCTGGTGTCACGCCCTCCCAGTG

TyrSerGlyProPro - - - LysThrGluLeuTrpPheSerTrpCysHisAlaLeuProVal
           ThrValAlaProArgGluArgGlnAsnCysGlyPheProGlyValThrProSerGlnCys 190       200       210       220       230       240
             |         |         |         |         |         |
           TGCAAATAAGGGCTGCTGTTTCGACGACACCGTTCGTGGGGTCCCCTGGTGCTTCTATCC

CysLys - - - GlyLeuLeuPheArgArgHisArgSerTrpGlyProLeuValLeuLeuSer
           AlaAsnLysGlyCysCysPheAspAspThrValArgGlyValProTrpCysPheTyrPro 250       260       270       280
             |         |         |         |
           TAATACCATCGACGTCCCTCCAGAAGTGTCTAAGGAATTC

- - - TyrHisArgArgProSerArgSerVal - - - GlyIle
           AsnThrIleAspValProProGluValSerLysGluPhe
```

Even though the NP5 DNA sequence is highly homologous to that of the SP2 DNA sequence, the amino acid sequence of NP5 is different from the amino acid sequence of the SP2. The open reading frame of NP5 starting at base 1 is different from the SP2 open reading frame starting at base 29, as shown in Table 2 above.

By epitope mapping using an Epitope Scanning Kit (Cambridge Research Biochemicals, Inc.), a series of overlapping amino acid hexamers were synthesized. The hexamers spanning the entire open reading frame of NP5 helped to determine that the only hexamer Mc5 bound to had the following amino acid sequence.

AspLeuArgProGlyPro

The amino acid sequence of this hexamer is only one part of the open reading frame of the NP5 region of extended homology to the amino acid sequence of the tandem repeat sequence that makes up a large part of the NPGP breast mucin (Gendler et al, J. Biol. Chem. 263: 12820 (1988). The native antigen for Mc5 is NPGP. By epitope mapping of the breast mucin tandem repeat amino acid sequence with a method similar to that described above (Gendler et al, supra) and using an Epitope Scanning Kit, it was found that Mc5 bound to only two overlapping amino acid hexamers.

AspThrArgProAlaPro, and

ThrArgProAlaProGly.

This binding thus occurs in the area where NP5 and the tandem repeat were found to have homology. The amino acids of the NP5 sequence that are homologous to the tandem repeat amino acids were underlined in the following portion of the NP5 sequence.

—AsPLeuArgProGlyProgly—

This example thus illustrates that the NP5 amino acid sequence portion of a fusion protein produced by the NP5 cDNA inserted into lambda/gt11 is novel, is synthesized in a bacteria infected with the phage carrying the cDNA sequence immediately after the β-galactosidase gene in the fusion DNA segment carried by the vector, and contains an epitope for Mc5 binding.

This NP5 fusion protein does not bind other monoclonal antibodies that bind to the tandem repeat amino acid sequence of NPGP, such as the Mc1, BrE1, BrE2 and/or BrE3 antibodies.

This example also illustrates the use of monoclonal antibodies to select a DNA fragment from a cDNA library that encodes a portion of a fusion protein that does not normally exist in nature but is produced in the bacteria as a result of being inserted after an auxiliary gene such as the β-galactosidase gene. Other auxiliary genes may be utilized instead of the β-galactosidase gene as is known in the art.

Example 7: Characteristics of NP4 cDNA Insert and Fusion Protein Encoded Therein Another example of a fusion protein comprising the epitopic region for one monoclonal antibody of a group of monoclonal antibodies that normally bind the same molecule in nature is NP4. The NP4 cDNA was isolated from a lambda/gt11 cDNA library in the same manner as discussed in Example 6 for NP5. The fusion protein produced by bacteria infected with phage DNA containing the NP4 cDNA insert contains a short region having the following amino acid sequence.

—HisThrArgProAlaLeu— with homology to the region of the tandem repeat.

—AspThrArgProAlaPro— of the NPGP breast mucin that binds monoclonal antibody BrE2.

Monoclonal antibodies Mc1, Mc5, BrE1 or BrE3 bind the tandem repeat but do not bind NP4. Furthermore, BrE3 competes with BrE2 for binding to the native NPGP breast mucin, but BrE3 does not bind the NP4 fusion protein.

An Epitope Scanning Kit was utilized to determine the epitope region on the tandem repeat amino acid sequence of the NPGP breast mucin for monoclonal antibodies BrE2 and BrE3. The results showed that both antibodies bound to the same four consecutive overlapping polypeptide hexamers with the following amino acid sequence being present in each hexamer.

ThrArgPro

The DNA sequence and the derived amino acid sequence of NP4 cDNA are given in Table 3 below.

TABLE 3

DNA Sequence of NP4 cDNA and Derived Amino Acid

```
        10        20        30        40        50        60
         |         |         |         |         |         |
GAATTCCATCACACCCGGCCGGCATTATGATTTTGTGTACTCTTGAAATGGTTATCTTTG

GluPheHisHisThrArgProAlaLeu - - -

70        80        90       100       110       120
         |         |         |         |         |         |
TGGATGATTTTTTTTTTTAAGCTGAAACTTACCTCATGAATAACTTGATTAAAGTAGTAG 130       140       150       160       170       180
         |         |         |         |         |         |
GTGATTAAAATTTCAATAGAATCAAATGAGACAAAAATTTTAAACTGACTCATTTGAGTT 190       200       210       220       230       240
         |         |         |         |         |         |
TCAACTTTACAGTCATTGACCATAAAGCACACTAAAAATGTAAGTTACTTTTAAATACAT 250       260
         |         |
ATAAAAATGGAATTC
```

The invention now being fully described, will be apparent to one of ordinary skill in the art that many changes and modifications can be made thereto without departing from the spirit or scope of the invention as set forth therein.

We claim:

1. An in vitro solid-phase, competitive assay for detecting the presence of a peptide analyte in a biological sample, comprising contacting a fusion protein comprising a first peptide and a second peptide with a first antibody or fragment thereof which specifically binds to a site of the first peptide which is absent from the second peptide while the second peptide remains free, and allowing the formation of complexes of the first peptide and the first antibody or fragment thereof, the first antibody or fragment thereof being covalently bound to a poly(amino acid)-coated solid support at a site other than the first peptide binding site;

adding thereto the biological sample suspected of comprising a peptide analyte, which binds specifically to a second antibody;

adding thereto, in the presence of the biological sample, a second antibody or fragment thereof specifically binding to the analyte peptide and to a site of the second peptide that is absent from the first peptide, and allowing the formation of free complexes of the analyte and the second antibody or fragment thereof and solid supported complexes of the fusion protein and the second antibody or fragment thereof; and determining the amount of solid supported second antibody or fragment thereof present and comparing it to the amount of solid supported antibody or fragment thereof present in a control assay conducted by substituting an equivalent volume of buffer for the biological sample, whereby when the amount of peptide analyte in the sample increases the amount of solid supported second antibody decreases.

2. The competitive assay of claim 1, wherein the fusion protein comprises unpurified fusion protein which becomes purified when added to the solid supported first antibody or fragment thereof.

3. The competitive assay of claim 1, wherein the first antibody comprises a monoclonal antibody.

4. The competitive assay of claim 1, wherein the second antibody comprises a monoclonal antibody.

5. The competitive assay of claim 4, wherein the monoclonal antibody comprises an anti-human mammary epithelial cell antigen antibody.

6. The competitive assay of claim 1, wherein the first peptide comprises beta-galactosidase or a fragment thereof.

7. The competitive assay of claim 1, wherein the amount of solid supported second antibody or fragment thereof is determined by adding a labeled molecule selectively binding the second antibody or fragment thereof and allowing the formation of solid supported complexes of fusion-protein labeled second antibody or fragment thereof; and removing unbound material.

8. The competitive assay of claim 1, wherein the poly(amino acid) coating the solid support comprises a ($C_1$–$C_3$) alkylated poly(amino acid).

9. The competitive assay of claim 1, wherein the second peptide comprises at least an amino acid sequence which specifically binds an antibody specific to a tissue marker.

10. The competitive assay of claim 9, wherein the tissue marker comprises a neoplastic cell marker or fragment thereof.

11. The competitive assay of claim 9, wherein the tissue marker comprises a tissue antigen selected from the group consisting of tissue differentiation antigens, epithelial antigens, tumor antigens, carcinoma antigens, carcinoma associated antigens, normal antigens and fragments thereof.

12. The competitive assay of claim 11, wherein the tumor antigens comprise tumor-associated antigens, tumor markers or fragments thereof; and the normal cellular antigens comprise cell surface antigens cytoplasmic antigens or fragments thereof.

13. The competitive assay of claim 1, wherein the second peptide of the fusion protein comprises the ThrArgPro amino acid segment.

14. The competitive assay of claim 1, wherein the second peptide comprises the amino acid sequence AspLeuArgProGlyPro.

15. The competitive assay of claim 14, wherein the fusion protein comprises the NP5 fusion protein.

16. The competitive assay of claim 1, wherein the second peptide comprises the amino acid sequence HisThrArgProAlaLeu.

17. The competitive assay of claim 16, wherein the fusion protein comprises the NP4 fusion protein.

18. The competitive assay of claim 1, further comprising separating the solid support bound complex from the remainder of the components prior to adding the biological sample, or prior to conducting the determining step.

19. The competitive assay of claim 1, further comprising adding thereto a labeled antibody-binding molecule and allowing the labeled molecule to bind the double antibody-fusion protein solid supported complex to form a labeled molecule-double antibody-fusion protein solid supported complex.

20. The competitive assay of claim 19, wherein the antibody binding molecule comprises radiolabeled antibodies or fragments thereof, protein A or protein G.

21. The competitive assay of claim 19, wherein the antibody binding molecule comprises fluorescently labeled antibodies or fragments thereof, protein A or protein G.

22. The competitive assay of claim 19, wherein the antibody binding molecule comprises enzyme labeled antibodies or fragments thereof, protein A or protein G; and the determining step is conducted by adding a substrate for the enzyme, determining the amount of substrate converted to product by the solid supported enzyme and comparing this value to the amount of substrate converted to product in a similar assay conducted by substituting an equivalent volume of buffer for the biological sample.

23. The competitive assay of claim 1, wherein the biological sample comprises about 0.00001 to 300 mg/ml protein; and the second antibody or fragment thereof comprises about 0.00001 to 0.06 mg/ml.

24. An in vitro solid-phase competitive assay for detecting the presence of a peptide analyte from a solid mammary tumor or metastasis thereof in a biological sample, comprising the method of claim 1, wherein the second peptide comprises at least an amino acid sequence which specifically binds an antibody specific to an epithelial mammary cell antigen;

the peptide analyte detected in the biological sample comprises a neoplastic tissue antigen from a solid mammary tumor or metastasis thereof or fragments thereof; and the second antibody or fragment thereof comprises an antibody or fragment thereof that specifically binds the epithelial mammary cell antigen.

25. An in vitro solid-phase competitive assay for detecting the presence of breast epithelial, carcinoembrionic or prostatic antigens, comprising the assay of claim 1, wherein the peptide analyte detected in the biological sample comprises breast epithelial, carcinoembrionic or static antigens or fragments thereof.

26. The assay of claim 1, wherein the second peptide comprises at least an amino acid sequence which specifically binds an antibody specific to an epithelial mammary cell antigen.

27. The competitive assay of claim 26, wherein the epithelial mammary cell peptide is selected from the group consisting of human milk fat globule antigens of about 70,000, 45,000–48,000, 150,000 and 400,000 apparent molecular weights, as determined by denaturing gel electrophoresis, and fragments thereof.

28. The competitive assay of claim 1, wherein the fusion protein comprises about 50 to 1,200 amino acids;

the first peptide comprises about 30 to 600 amino acids; and the second peptide comprises about 7 to 600 amino acids.

29. A kit for detecting the presence of a peptide analyte from a solid tumor or metastasis thereof in a biological sample, comprising a fusion protein of about 50 to 1,200 amino acids comprising a first peptide of about 30 to 600 amino acids and a second peptide of about 7 to 600 amino acids;

a first antibody or fragment thereof specifically binding to a site of the first peptide which is absent from the second peptide;

a second antibody or fragment thereof specifically binding to a peptide analyte to be detected and to a site of the second peptide not present in the first peptide; and instructions for its use.

30. The kit of claim 29, further comprising a polyamino acid coated solid support; and wherein the first antibody or fragment thereof is covalently bound to the poly(amino acid) coated solid support at a site other than the first peptide binding site.

31. The kit of claim 30, wherein the poly(amino acid) coating the solid support comprises a ($C_1$–$C_3$) alkylated poly(amino acid).

32. The kit of claim 29, further comprising a solid support;

a poly(amino acid); and instructions for coating the solid support with the poly(amino acid).

33. The kit of claim 32, wherein the poly(amino acid) comprises a ($C_1$–$C_3$)alkylated poly (amino acid).

34. The kit of claim 29, wherein the first antibody comprises a monoclonal antibody.

35. The kit of claim 29, wherein the second antibody comprises a monoclonal antibody.

36. The kit of claim 29, wherein the first peptide comprises beta-galactosidase or a fragment thereof.

37. The kit of claim 29, further comprising a detection means for detecting the second antibody or fragment thereof.

38. The kit of claim 37, whereni the detection means comprises an antibody-binding molecule.

39. The kit of claim 38, wherein the molecule may be radiolabeled, fluorescently labeled or enzyme labeled.

40. The kit of claim 38, wherein the antibody-binding molecule is selected from the group consisting of antibodies or fragments thereof, protein A or protein G.

41. The kit of claim 29, wherein the second peptide comprises the amino acid sequence ThrArgPro.

42. The kit of claim 29, wherein the second peptide comprises the amino acid sequence AspLeuArgProGlyPro.

43. The kit of claim 42, wherein the fusion protein comprises the NP5 fusion protein.

44. The kit of claim 29, wherein the second peptide comprises the amino acid sequence HisThrArgProAlaLeu.

45. The kit of claim 44, wherein the fusion protein comprises the NP4 fusion protein.

46. The kit of claim 29, wherein the second peptide comprises at least an amino acid sequence which specifically binds an antibody specific to an epithelial mammary cell antigen.

47. The kit of claim 46, wherein the epithelial mammary cell peptide of the fusion protein is selected from the group consisting of human milk fat globule antigens of about 70,000, 45,000–48,000, 150,000 and 400,000 apparent molecular weights, as determined by denaturing gel electrophoresis, and fragments thereof.

48. The kit of claim 35, wherein the monoclonal antibody comprises an anti-human mammary epithelial cell antigen antibody.

49. The kit of claim 29, wherein the second peptide comprises at least an amino acid sequence which specifically binds an antibody specific to a normal or neoplastic tissue marker or fragment thereof.

50. The kit of claim 49, wherein the tissue marker comprises a tissue antigen selected from the group consisting of tissue differentiation antigens, epithelial antigens, tumor antigens, carcinoma antigens, carcinoma associated antigens, normal cellular antigens and fragments thereof.

51. The kit of claim 50, wherein the tumor antigens comprise tumor-associated antigens, tumor markers or fragments thereof; and the normal cellular antigens comprise cell surface or cytoplasmic antigens or fragments thereof.

* * * * *